(12) United States Patent
Alba et al.

(10) Patent No.: US 9,763,893 B2
(45) Date of Patent: Sep. 19, 2017

(54) MONOPOLYMER MULTIFUNCTIONAL SEQUENCED CAST POLYURETHANE MATRIX AND PRODUCTION METHOD

(71) Applicant: AB7 INNOVATION S.A.S.U., Deyme (FR)

(72) Inventors: Aurelie Alba, Noueilles (FR); Arnaud Vilbert, Baziege (FR); Rene Chelle, Crepiac (FR)

(73) Assignee: AB7 INNOVATION S.A.S.U., Deyme (FR)

( * ) Notice: Subject to any disclaimer, the term of this patent is extended or adjusted under 35 U.S.C. 154(b) by 0 days.

(21) Appl. No.: 14/408,413

(22) PCT Filed: May 27, 2013

(86) PCT No.: PCT/FR2013/000134
§ 371 (c)(1),
(2) Date: Dec. 16, 2014

(87) PCT Pub. No.: WO2014/001653
PCT Pub. Date: Jan. 3, 2014

(65) Prior Publication Data
US 2015/0190350 A1    Jul. 9, 2015

(30) Foreign Application Priority Data

Jun. 26, 2012   (FR) .................................... 12 01794

(51) Int. Cl.
| | | |
|---|---|---|
| C08G 18/76 | (2006.01) | |
| A61K 9/70 | (2006.01) | |
| A01N 25/10 | (2006.01) | |
| C08G 18/48 | (2006.01) | |
| C09J 175/04 | (2006.01) | |
| A43B 1/00 | (2006.01) | |
| A43B 7/14 | (2006.01) | |
| A01N 25/24 | (2006.01) | |
| B29C 39/00 | (2006.01) | |
| C11B 9/00 | (2006.01) | |
| B29K 29/00 | (2006.01) | |
| B29K 75/00 | (2006.01) | |
| B29L 9/00 | (2006.01) | |

(52) U.S. Cl.
CPC ............ *A61K 9/7084* (2013.01); *A01N 25/10* (2013.01); *A01N 25/24* (2013.01); *A43B 1/0045* (2013.01); *A43B 7/1455* (2013.01); *A61K 9/7069* (2013.01); *B29C 39/003* (2013.01); *C08G 18/4829* (2013.01); *C08G 18/7671* (2013.01); *C09J 175/04* (2013.01); *C11B 9/00* (2013.01); *B29K 2029/04* (2013.01); *B29K 2075/00* (2013.01); *B29L 2009/00* (2013.01); *C09J 2475/00* (2013.01)

(58) Field of Classification Search
CPC .... A61K 9/7084; A61K 9/7069; A01N 25/24; A01N 25/10; B29C 39/003; C08G 18/7671; C08G 18/4829; C09J 175/04; C09J 2475/00
See application file for complete search history.

(56) References Cited

U.S. PATENT DOCUMENTS

| | | | |
|---|---|---|---|
| 5,662,926 A | 9/1997 | Wick et al. | |
| 2007/0003745 A1* | 1/2007 | Edstrom | C08G 18/482 428/217 |
| 2009/0143280 A1* | 6/2009 | Kristiansen | A61K 31/70 514/1.1 |

FOREIGN PATENT DOCUMENTS

| | | |
|---|---|---|
| EP | 0212681 A2 | 3/1987 |
| WO | WO0059483 A2 | 10/2000 |

OTHER PUBLICATIONS

International Search Report of PCT/FR2013/000134; Nov. 11, 2013; Sylvie Scheuer.

* cited by examiner

*Primary Examiner* — Michael L Leonard
(74) *Attorney, Agent, or Firm* — Klauber & Jackson LLC

(57) ABSTRACT

The invention relates to a monopolymer multifunctional sequenced cast polyurethane matrix produced simply and efficiently, by sequentially pouring various isocyanate/polyol complex phase solutions successively into a mould with alternating solidification of said phase solutions according to a defined order and respecting the polymerisation stage (after the pot life and before the demoulding time) of the sequence preceding the one being cast, so as to end with the casting of the last phase solution that will go up to the demoulding time thereof and thereby finish the polymerisation of the whole of the matrix. It is loaded, in its "reservoir" sequences, with naturally originating or synthesised transdermally penetrating or volatile active substances. They are medicating and therapeutic, cosmetic, phytosanitary or wellness substances, repellents, attractants, pheromones, biocides, perfumes or deodorants. At least two active substances can be loaded into the same matrix in order to act unidirectionally or in opposite directions. Said matrix is used to form different devices that adhere to the skin or any other surface, in order to deliver at least one substance in a controlled manner. Said devices are patches, patches with a plurality of active substances, replaceable plasters stuck to a textile support, active heel pads and ball pads for shoes, pheromone cards for controlling insects, self-adhesive insecticide attractant cards, or other devices equivalent in terms of structure and function.

4 Claims, No Drawings

MONOPOLYMER MULTIFUNCTIONAL SEQUENCED CAST POLYURETHANE MATRIX AND PRODUCTION METHOD

This application is a U.S. National Phase application under 35 USC §371 of PCT/FR2013/000134, filed May 27, 2013, which claims priority from and the benefit of French Patent Application No. FR 1 201 794, filed Jun. 26, 2012. Applicant claims the benefits of 35 U.S.C. §120 to the PCT application and priority under 35 U.S.C. §119 to the French patent application, and the entire disclosures of both applications are incorporated herein by reference in their entireties.

This invention concerns a monopolymer multifunctional sequenced cast polyurethane matrix, which concomitantly fulfils the Support or Support-Barrier, active substance reservoir and adhesive functions; the said functions being obtained thanks to a sequential pouring process of the polymer formulated according to phases which induce the characteristics corresponding to the various functions indicated for each phase to make up the said matrix forming an active substance distribution device.

The active substance distribution matrix devices, such as patches, plasters, and others, divulgated, for example, by the patent EP0341202 and the patent application US2011038904, are generally a stratified structure organised mainly into three essential layers:

- a support or covering layer in a polymer impermeable to the active substance, generally made of polyethylene terephthalate (PET), polypropylene (PP), polyvinyl chloride (PVC), polybutylene terephthalate (PBT), polyethylene (PE), an ethylene vinyl acetate copolymer (EVA), or even polyurethane (PU); this support layer can also act as a barrier to the active substances;
- a reservoir layer in which the active substances are stored, which can be made of a polyurethane (PU) gel to take advantage of the regularity of the release of the active substances brought by this polymer, in gelatine, polyvinyl alcohol polymer, methylcellulose, or one of the block copolymers, or even other crosslinked polymers which can store an active substance to release it slowly. The active substances are incorporated by a hot melt of the polymer or by a solubilisation of the said polymer with an organic solvent such as described in the patents EP1169025 and EP0416842;
- a self-adhesive layer composed of polymers which have adhesive properties such as those of polysiloxanes, polyacrylates, silicones, vinyl polymers, vinyl acetate, ethylene vinyl acetate copolymer, polyisobutylenes, polyurethanes, natural rubbers or natural and synthetic rubbers described in various ways by the patents EP1169025, EP0416842, EP0836506, EP0563507 and EP2324859, to mention only those, that is, substances allowing to bond the device to a given surface or onto the skin.

The realization of such a device is technically complex. In fact, it has the disadvantage of being practically impossible to realize because the compatibility of the various materials used has to be taken into account, as well as the multiplicity of the technological operations to be executed. The good operation of the resulting devices depends on the properties of each of the layers of the various polymers on which depend in turn the functions attributed to them [EP 2 191 810]. Each layer is separately prepared according to a special process, which multiplies the technological operations and requirements, including in terms of the tools used.

The support, a film made of PET, PP, PVC, PBT, PE or even EVA, requires a hot extrusion, a high energy consumer, or a solubilisation in a solvent, which has to be recycled or eliminated to account for the environmental impact. In case the film is made of polyurethane, we have examples of the application of the application patent WO 2011136330, which describes an extruded film with a thickness of 1 to 10 µm, the application patent EP 2 324 803 A2, which uses a film obtained by melt blowing, while the application of the application patent EP0212681 A2 divulgates a film obtained by a melting of polyurethane by actinic radiation.

In case the reservoir is made of polyurethane, it is generally designed individually before it is mounted in a multilayer system. Thus, the patent EP1169025 describes a device which includes a reservoir layer elaborated from melted polyurethane granules to be mixed between 40° C. and 90° C. with the fentanyl drug. The patent EP1634566 divulgates a reservoir for which the polyurethane structure itself is modified by the grafting of hydrophilic ethylene oxide segments, as well as hydrophobic propylene oxide segments, to incorporate the vitamin C. Here again, a large expenditure of energy is necessary. In addition, the hot treatment of the polymer is a source of deterioration or denaturation of the thermolabile active substances.

In case the adhesive layer is made of polyurethane, it is designed thanks to the addition of silicone or an alkyl methacrylate copolymer such as describes by the patent EP2191810. This is an additional operation which requires a certain dosing precision of the various materials used.

To minimise the difficulty inherent to the multilayer system, the tendency in practice is to reduce the number of layers of the stratified device: thus, the bi-functionalization of the reservoir layer into a self-adhesive layer reservoir. To do this, the polyurethane is associated with acrylic polymers [EP2001424, EP2431437, EP1875898, EP2412390, EP0341202, U.S. Pat. No. 6,727,401]. The patent EP1263830 describes an adhesive matrix made of a polyurethane obtained from an aqueous system by using two polyols with a molecular weight MW<2000 for one and MW>2000 for the other. The sum of the two polyols exceeds the isocyanate to obtain called subindex polyurethane. But the obtained adhesive matrix is applicable to a dispersion substrate only by heating it for 10 minutes at 70° C.

The self-adhesive layer made of polyurethane generally obtained as described effectively sticks on both sides. This necessitates, when only one sticky side is desired, that the other side of the said self-adhesive layer be covered with a barrier film made of polyvinyl alcohol polymer (PVA) or an ethylene vinyl acetate copolymer (EVA), offering a non-adhesive side as described by the application patent EP 1 634 566 A1.

A person skilled in the art knows that the adhesive effect of a polyurethane can be acquired by acting on the stoichiometry of the polymerisation reaction between the isocyanate and the polyol(s), which is expressed here by the ratio OH/NCO. When the isocyanate is in excess, the stoichiometry is less than 1. An evolving adhesive effect can be obtained by the reaction of the free NCO radicals. On the other hand, when the OH radicals of the polyol(s) are in excess, the stoichiometry is greater than 1. A stable, effective adhesive effect is obtained.

There is indeed a need to provide a new technical design that allows obtaining a monopolymer multifunctional cast polyurethane matrix, thereby replacing complex stratified structures from which active substance distributor self-adhesive devices are elaborated.

To get a better understanding of the invention, the phrase <<monopolymer multifunctional sequenced cast polyurethane matrix>> means a matrix obtained by mixing a liquid polyol complex of a variable composition with a liquid isocyanate to obtain a liquid phase solution. The said phase solution is sequentially poured into a mould to obtain a succession of sequences, making sure that the phase solution poured on the previous sequence is poured before the polymerisation of the said previous sequence is terminated to obtain a copolymerisation at the interface of the two sequences.

The term <<polyol complex>> means the solution of the polyol(s) with the various technical additives (catalyst, elongator, plasticizer, degazing agent, ultraviolet stabilizer, etc.) and possibly the active substance(s). Its composition varies in accordance with function and the desired characteristics for the sequence to be polymerised.

The term <<phase solution>> means the mixture of the liquid polyol complex with the liquid isocyanate.

The term <<sequence>> means the phase solution in polymerisation in the mould. The <<sequence>> is determined by both the polyol complex's composition and the stoichiometry of the phase solution.

The term <<matrix profile>> means the organisation according to the order of succession of the various sequences making up the matrix.

The term <<pot life>> means the polymerisation level characterised by a seam stretching of the gel which begins forming from the phase solution. The pot life is experimentally determined and expressed in time units, generally in seconds.

The term <<demoulding time>> means the level of polymerisation from which the removal from the mould of the polymer die becomes possible without damaging the moulded device. The demoulding time is experimentally determined and expressed in time units.

One of the objectives of the invention is to realize a monopolymer multifunctional sequenced cast polyurethane matrix, which concomitantly fulfils the support or support-barrier, reservoir of active substance(s) and adhesive functions according to a desired arrangement of the functionalised sequences defining a particular profile of the said matrix.

The applicant discovered surprisingly that such matrix could be obtained simply and efficiently, by sequentially pouring various isocyanate/polyol complex successively into a mould with alternating solidification of said phase solutions according to a define order and respecting the polymerization stage (after the pot life and before the demoulting time) of the sequence preceding the one being cast, so as to end with the casting of the last solution phase that will go up to the demoulding time thereof and thereby finish the polymerization of the whole of the matrix.

According to an aspect of the invention, the monopolymer multifunctional sequenced cast polyurethane matrix presents a uniqueness or a structural continuity ensured by the state of copolymerisation at the interface of the successive functional sequences.

According to the invention, the matrix is loaded in its <<reservoir>> sequences, with naturally originating or synthesized transdermally penetrating or volatile active substances. The said active substances, according to the invention, are medicating and therapeutic, cosmetic, phytosanitary or wellness substances, repellents, attractants, pheromones, biocides, perfumes or odorants.

According to an embodiment of the invention, the active substance(s) represent(s) between 0.01% and 40% by weight of the monopolymer multifunctional sequenced cast polyurethane matrix.

In fact, according to the invention, the same matrix can contain several active substances of a different nature belonging to differ rent fields of activity and able to act either in the same direction or in opposite directions. For example, a soothing perfume of the field of atmospheric activity can be associated in the same matrix with a pain relief active substance of the field of transdermal activity. The two active substances are loaded in different <<reservoir>> sequences.

Likewise, according to an embodiment of the invention, two or more active substances belonging to the same field of activity loaded in the different <<reservoir>> sequences in the same matrix can act unidirectionally, but at different speeds and flow rates.

According to the invention, said matrix is used to form different devices that adhere to the skin or any other surface, in order to deliver at least one substance in a controlled manner.

According to the invention, said devices are patches, patches with a plurality of active substances with several active substances having an unidirectional actions or actions in opposite directions (example: one to the skin and the other to the atmosphere), replaceable plasters stuck to a textile support (harness, bandages, underwear), active heel pads and ball pads for shoes, pheromone cards for controlling insects, self-adhesive insecticide attractant cards, or other devices equivalents in terms of structure and function.

For this purpose, the monopolymer multifunctional sequenced cast polyurethane matrix according to the invention has a thickness which evolves from a film 10 to 100 micrometer thick to a polymer block of several centimetres in which each sequence can have a different thickness. For example, the reservoir sequence thickness will vary according to the volume of active substance(s) to be stored and the desired activity duration.

Another objective of the invention is to provide a process to elaborate for the monopolymer multifunctional sequenced cast polyurethane matrix.

Thus, according to the invention, the preparation process of a monopolymer multifunctional sequenced cast polyurethane matrix at room temperature includes the following steps:

a). preparation of the polyol complex 1, which consists of mixing the solution of the various additives, and, if appropriate, the active substance(s) corresponding to the function of the future sequence 1 and the polyol(s);

b). preparation of the phase solution 1, which consists of mixing the polyol complex 1 obtained in step a)—with the isocyanate according to the stoichiometry corresponding to the function of the future sequence 1;

c). pouring of the said phase solution 1 in the mould to obtain the sequence 1 in conformity with the desired thickness of the said sequence 1;

d). preparation of the polyol complex 2, which consists of mixing the solution of the various additives, and, if appropriate, the active substance(s) corresponding to the function of the future sequence 2 and the polyol(s);

e). preparation of the phase solution 2, which consists of mixing the polyol complex 2 obtained in step d)—with the isocyanate according to the stoichiometry corresponding to the function of the future sequence 2;

f). pouring of the phase solution 2 in the mould to obtain the sequence 2 in conformity with the desired thickness of the said sequence 2 on the sequence 1, which has exceeded the pot life, but which has not attained the demoulding time to allow a copolymerisation at the interface of the two sequences;

g). repeat the steps a)—to f)—to obtain an <<n>> sequences multifunctional cast polyurethane matrix, the last and/or the first sequence according to the matrix's selected profile being a sequence at least adhesive in which the phase solution of the polyol complex with the isocyanate has a stoichiometry greater than 1;

h). let the polymerisation of the last sequence terminate up to its demoulding time and therefore up to the polymerisation of the whole of the matrix;

i). remove the formed monopolymer multifunctional sequenced matrix from the mould;

j). package the said matrix in a sealed, tight, and impermeable pocket.

According to the process of the invention, the surface of the sequence under total polymerisation reaction offers still free reagent radicals with which immediately react the radicals brought by the phase solution being poured in order to generate a copolymerisation on this interface when the said phase solution is polymerised in turn to generate a sequence. The said sequence will thus form an assembly with the previous sequence without as such causing any interpenetration of the two sequences. The continuity and therefore the uniqueness of the monopolymer multifunctional sequenced cast polyurethane matrix is conditioned by the phenomenon of copolymerisation of the successive functional sequences at their contact interfaces which are in polymerization reaction in progress.

According to an embodiment of the invention, the Support sequence can be impermeabilized to become a Support-Barrier vis-à-vis the active substances by adding resin(s) with a low molecular weight and/or inert loads.

Precisely, according to the invention, the process to elaborate of the monopolymer multifunctional sequenced cast polyurethane matrix is realized with the main reactive materials of polymerisation, which are:

a). the isocyanate selected from among the isocyanates with at least two functionalities of an aromatic or aliphatic structure;

b). the polyol(s) selected from among those with at least two hydroxyl functionalities, preferentially with a long chain and, depending on the case, with a short chain, based on polyesters, polyethers, polythioethers, polyacetals, polycarbonates, polyesteramides, naturally hydrolysed or modified vegetable oils or the mixture thereof. The polyols can be replaced according to the same reactivity considerations as with isocyanate, polyamines having at least two amine functionalities selected from among the aliphatic or aromatic polyetheramines and under some conditions by water.

The polyol complex formulation additives according to the invention are selected according to the type of function which each sequence will fulfil, and the globally desired characteristics of the device to be formed which are:

a). the catalyst selected from among the organometallic solutions, preferentially bismuth, or tertiary amine solutions;

b). the degazing agent selected from among the polymers of polysiloxanes, the polymers of methyl alkyl polysiloxanes or a mixture thereof;

c). the plasticizer selected from among the solutions of ester benzoate, the alkyl phosphates, as well as those known by a person skilled in the art;

d). the impermeabilizer selected from among the resins of low molecular weight or inert loads, preferentially of a siliceous nature;

e). the ultraviolet stabilizers selected from among those known by a person skilled in the art and the other stabilizers selected from among the phenolic antioxidants type BHT (Butylated hydroxytoluene) or BHA (Butylated hydroxyanisol), the redox antioxidants type HALS (Hindered Amine Light Stabilizer) with piperidine pattern, the phosphite antioxidants, the formamidine antioxidants, the benzotriazole antioxidants, the benzophenone antioxidants or a mixture thereof;

f). the dye of the polyurethanes known by a person skilled in the art.

According to an embodiment of the invention, the monopolymer multifunction sequence cast polyurethane matrix offers several combinational possibilities of functional sequences to obtain profiles which allow a great mastery of the release of the active substances control, particularly in the following cases:

A). Support/Reservoir/Adhesive to allow the active substance in the reservoir sequence to traverse the adhesive sequence for a transdermal delivery, for example;

B). Reservoir 1/Support-Barrier/Reservoir 2-Adhesive for two different active substances: the active substance of the Reservoir1, which is intended to be released by volatility into the atmosphere, and the active substance of the Reservoir 2 which is intended for a transdermal delivery;

C). Support/Reservoir-Adhesive for an active substance with a fast transdermal release;

D). Reservoir/Support-Barrier/Adhesive for a volatile active substance with a release into the atmosphere and which must not come in contact with the skin;

E). Support/Reservoir 1/Reservoir 2/Adhesive for two different active substances respectively in the Reservoir 1 and Reservoir 2 sequences with deferred speed and flow rate by transdermal delivery;

F). Support/Reservoir 1/Reservoir 2-Adhesive for two different active substances respectively in the Reservoir 1 and Reservoir 2-Adhesive sequences with differentiated speed and release flow rate by transdermal delivery, but with a highly accelerated release of the active substance of the Reservoir 2-Adhesive.

The process according to the invention brings the following technological advantages:

a). simplification of the implementation of the various said matrix profiles;

b). significant pushed automation possibilities for the production of devices;

c). large possibilities for the forms of devices and therefore utilisations;

d). large possibilities for the adjustment of the mechanical functionalities and active substances;

e). preservation of the quality of the active substances due to the treatment at room temperature;

f). no solvents for the preservation of the nature and energy saving for their elimination;

g). wide range of usable active substances thanks to the large storage capacities of the cast polyurethane for both lipophilic substances and hydrophilic substances of a natural or synthesis nature.

A pouring machine, which allows implementing the process according to the invention, consists of at least two reservoirs, one for the polyol complex and the other for the isocyanate, both equipped with flow rate regulators and a system to thrust the liquids under low pressure toward a mixer, which allows distributing the liquid phase solution in the polymerisation mould for the forming of the desired device.

According to an embodiment of the invention, the production of devices in a monopolymer multifunctional sequenced cast polyurethane matrix is realized in a pouring machine whose configuration (production capacity, number of liquid reservoirs, flow rate of the liquids, thrust pressure of the liquids, thrust order of the liquids according to the reservoirs, turbine profile, nature of the mould(s)), is adapted by a person skilled in the art, and is equipped with an electronic supervision device.

EXAMPLES

The following examples are used to illustrate the invention without being exhaustive and without limiting the scope which extends to equivalent devices in terms of structure and function.

Example 1

Self-Adhesive Pain Relief Patch in the Matrix with a <<Support/Reservoir-Adhesive>> Profile For the making of a monopolymer matrix loaded in active substance offering a self-adhesive function on only one side of a patch, a matrix profile organised into a succession of two sequences: a support sequence and an adhesive reservoir sequence loaded with a pain relief active substance.

To do this, the following products are available:
a long chain ether-based polyol, more precisely, a polypropylene glycol (PPG) of MW=4800 and having three functionalities. This polyol is produced by REPSOL and marketed under the brand ALCUPOL® C-3531;
an aromatic diisocyanate of type 4,4'-methylene diphenyl diisocyanate (MDI) of MW=344 and presenting a ratio of NCO=24.4%, marketed by HUNTSMAN under the brand SUPRASEC® 2029;
a degazing agent, which is a solution of polymers and polysiloxanes, produced by BYK CHEMIE and marketed under the brand BYK 088;
a plasticizer, which is a mixture of benzoate esters, marketed by VELSICOL under the brand BENZO-FLEX® 9-88 SG;
a catalyst agent, which is a bismuth neodecanoate complex, marketed by SHEPHERD under the brand BICAT® 8124M;
a mixture of essential oils with a pain relief action, marketed by INTERAXION.

The following equipment is available:
an open cylindrical reactor of 1 liter;
a metallic agitator equipped with a 25 cm long shaft and a 6 cm in diameter, disk at its end. The agitator is driven by a variable speed electric motor;
a mould made of polypropylene (PP), whose footprint is an open parallelepiped of 7 cm×5 cm on the sides and 5 mm in depth.

Procedure: All the operations are performed at room temperature.

A)—Preparation of the <<Support>> Phase Solution of a Stoichiometry OH/NCO=1

The catalyst is prepared by pouring a solution of 5% BICAT® 8124M in the plasticizer.

Then the following are successively introduced in the reactor:
3.06 parts by weight of the catalyst solution;
1.24 parts by weight of the degazing agent and
86.42 parts by weight of the long chain polyol.

All this is agitated at 1300 rpm for 30 seconds. The polyol complex is obtained;

In the said polyol complex, 9.27 parts by weight of isocyanate are added according to a stoichiometry OH/NCO=1, and agitated at 1300 rpm for 30 seconds to obtain the phase solution;

The said phase solution obtained is poured in the mould over a thickness of 1 mm, and the polymerisation reaction is allowed to continue to constitute the <<support>> sequence.

B)—Preparation of the <<Reservoir-Adhesive>> Phase Solution of a Stoichiometry OH/NCO=1.6

In parallel with operation A), the polyol complex is modified by associating in the reactor:
2.55 parts by weight of the catalyst solution;
1.03 parts by weight of the degazing agent;
16.86 parts by weight of the mixture of essential oils with a pain relief action, the said active substance, and
74.56 parts by weight of the long chain polyol of operation A).

All this is agitated at 1300 rpm for 30 seconds. The polyol complex loaded with the pain relief active substance is obtained;

In the said loaded polyol complex obtained, 4.99 parts by weight of isocyanate are added according to a stoichiometry OH/NCO=1.6 and agitated at 1300 rpm for 30 seconds. The phase solution charged with the active substance is obtained;

The said phase solution is poured to a thickness of 1 mm on the <<Support>> sequence which has exceeded the <<pot life>>, but has not attained the demoulding time and therefore is still in polymerization reaction in progress;

The polymerisation is allowed to continue in order to constitute the <<Reservoir-Adhesive>> sequence;

The thus obtained patch is removed from the mould when the demoulding time of the last <<Reservoir-Adhesive>> sequence is attained.

The 2 mm thick patch obtained is very flexible and adhesive on the side of the <<Reservoir-Adhesive>> sequence and not adhesive on the side of the <<Support>> sequence. The said self-adhesive patch is intended for the treatment of muscular pains. It is glued directly on the skin.

Example 2

Soothing Self-Adhesive Plaster in a Matrix with a <<Reservoir-Support /Adhesive>> Profile This example illustrates the making of a monopolymer matrix loaded in active substance offering the self-adhesive function of a plaster on only one side according to a matrix profile organised in a succession of two sequences: a reservoir support sequence loaded with the soothing active substance and an adhesive sequence.

Another long chain ether-based polyol (PPG) of MW=2000 and having two functionalities is associated with the isocyanate and the long chain polyol of example 1. This long chain polyol is also produced by REPSOL and marketed under the brand ALCUPOL® D-2021.

A stabilizer composed of a mixture of formamidines is also available and marketed by ZIKO under the brand ZICA-CUV®, as well as a soothing perfume marketed by ROBERTET under the brand ELISIA®+.

The same equipment is available as that used in example 1 and a mould whose footprint is an open parallelepiped of 14 cm×10 cm on the sides and 5 mm in depth.

Procedure: The operations are performed according to a procedure similar to that of example 1 and the catalyst solution is prepared like in example 1.

A)—Preparation of the <<Reservoir-Support>> Phase Solution of Stoichiometry OH/NCO=1

The following are successively introduced in the reactor:
2.97 parts by weight of the catalyst solution;
0.15 of a part by weight of the stabilizer;
1.02 parts by weight of the degazing agent;
3.06 parts by weight of the perfume with a soothing action, perfume is called active substance;
49.84 parts by weight of the long chain polyol (ALCUPOL® C-3135) and
31.09 parts by weight of the long chain polyol (ALCUPOL® D-2021)

All this is agitated at 1300 rpm for 30 seconds. The polyol complex loaded with the soothing active substance is obtained;

In the said polyol complex obtained, 11.87 parts by weight of isocyanate are added according to a stoichiometry OH/NCO=1, and agitated at 1300 rpm for 30 seconds. The phase solution loaded with the active substance is obtained;

The said phase solution obtained is poured in the mould over a thickness of 1 mm, and the polymerisation reaction is allowed to continue to constitute the <<Reservoir-Support>> sequence.

B)—Preparation of the <<Adhesive>> Phase Solution of a Stoichiometry OH/NCO=1.4

In parallel with operation A), the polyol complex is modified by associating in the reactor:
3.06 parts by weight of the catalyst solution;
0.16 of a part by weight of the stabilizer;
1.06 parts by weight of the degazing agent;
53.54 parts by weight of the long chain polyol of operation A) (ALCUPOL® C-3531) and
33.83 parts by weight of the long chain polyol of operation A) (ALCUPOL® D-2021).

All this is agitated at 1300 rpm for 30 seconds. The polyol complex is obtained;

In the said polyol complex obtained, 8.25 parts by weight of isocyanate are added according to a stoichiometry OH/NCO=1.4 and agitated at 1300 rpm for 30 seconds. The phase solution is obtained;

The said phase solution obtained is poured to a thickness of 1 mm on the <<Reservoir-Support>> sequence which has exceeded the pot life, but which has still not attained the demoulting time;

Polymerisation is allowed to continue in order to constitute the <<Adhesive>> sequence;

The thus obtained plaster is removed from the mould when the demoulting time of the said <<Adhesive>> sequence is attained.

The soothing plaster obtained is very flexible and has a thickness of 2 mm. The plaster is stuck with its adhesive side to a textile harness. It is intended for the treatment of anxiety in adult dogs thanks to a harness fixed around the dog's waist—plaster against coat.

Example 3

Self-Adhesive Perfuming Pad for Shoe Toe Tips in a Matrix with a <<Reservoir/Support-Barrier/Adhesive>> Profile This example illustrates the making of a monopolymer matrix loaded in active substance offering a self-adhesive function of a pad for shoes on only one side according to a matrix profile organised in a succession of three sequences: a reservoir sequence loaded with the active substance, a support barrier sequence and an adhesive sequence.

Another long chain polyol ALCUPOL® D-2021 is associated with the isocyanate and the long chain polyol of example 1. The following are also available:
a degazing agent BYK 088,
a stabilizer ZICA-CUV®,
a perfume marketed by CREATIONS & PARFUM under the brand BSG®51774.

The same equipment is available as that used in example 1 as well as a metal mould whose footprint is a pad for a foot tip 9.5 cm long, 7 cm wide and 3 mm in depth.

Procedure: The operations are performed according to a procedure similar to that of example 1 and the catalyst solution is prepared like in example 1.

A)—Preparation of the <<Reservoir>> Phase Solution of a Stoichiometry OH/NCO=1

The following are successively introduced in the reactor:
2.75 parts by weight of the catalyst solution;
0.13 of a part by weight of the stabilizer;
0.91 of a part by weight of the degazing agent;
4.58 parts by weight of the perfume called active substance and
82.76 parts by weight of the long chain polyol (ALCUPOL® C-3531).

All this is agitated at 1300 rpm for 30 seconds. The polyol complex loaded with the active substance is obtained;

In the said polyol complex obtained, 8.87 parts by weight of isocyanate are added according to a stoichiometry NCO/OH=1, and agitated at 1300 rpm for 30 seconds. The phase solution loaded with the active substance is obtained;

The said phase solution obtained is poured in the mould over a thickness of 1 mm, and the polymerisation reaction is allowed to continue to constitute the <<Reservoir>> sequence.

B)—Preparation of the <<Support-Barrier>> Phase Solution of a Stoichiometry OH/NCO=1

In parallel with operation A)—, the polyol complex is modified by associating in the reactor:
1.95 parts by weight of the catalyst solution;
0.49 of a part by weight of the degazing agent and
59.65 parts by weight of the long chain polyol (ALCUPOL® C-3531)

All this is agitated at 1300 rpm for 30 seconds. The polyol complex is obtained;

In the said polyol complex, 37.92 parts by weight of isocyanate are added according to a stoichiometry OH/NCO=1 and agitated at 1300 rpm for 30 seconds. The phase solution is obtained;

The said phase solution obtained is poured to a thickness of 1 mm on the <<Reservoir>> sequence which has exceeded the pot life, but which has still not attained the demoulting time, and the polymerisation reaction is allowed to continue to constitute the <<Support-Barrier>> sequence.

C)—Preparation of the <<Adhesive>> Phase Solution of a Stoichiometry OH/NCO=1.4

In parallel with operation B), the polyol complex is modified by associating in the reactor:
  3.06 parts by weight of the catalyst solution;
  0.16 of a part by weight of the stabilizer;
  1.06 parts by weight of the degazing agent;
  53.54 parts by weight of the long chain polyol of operation A) (ALCUPOL® C-3531) and
  33.83 parts by weight of the long chain polyol of operation A) (ALCUPOL® D-2021).
All this is agitated at 1300 rpm for 30 seconds. The polyol complex is obtained;
In the said polyol complex obtained, 8.25 parts by weight of isocyanate are added according to a stoichiometry OH/NCO=1.4 and agitated at 1300 rpm for 30 seconds. The phase solution is obtained;
The said phase solution obtained is poured to a thickness of 1 mm on the <<Support Barrier>> sequence which has exceeded the pot life, but which has still not attained the demoulting time;
Polymerisation reaction is allowed to continue in order to constitute the <<Adhesive>> sequence;
The thus obtained pad is removed from the mould when the demoulding time of the said <<Adhesive>> sequence is attained.

The 3 mm thick perfuming pad obtained is flexible and self-adhesive. The said pad adheres to the shoe sole on the side of the adhesive sequence. It also allows perfuming the shoe's interior. Due to the mechanical properties of the matrix (flexibility, elasticity and damping), the pad brings comfort to the wearer.

Example 4

Self-Adhesive Well-being and Slimming-Down Patch in a Matrix with a <<Reservoir/Support-Barrier/Adhesive-Reservoir>> Profile This example illustrates the making of a monopolymer matrix with a double activity, an activity with an atmospheric effect and an activity with a transdermal effect, brought by a patch self-adhesive on only one side. The said patch has a matrix profile organised into a succession of three sequences: a reservoir sequence loaded with a volatile active substance, a support barrier sequence and a reservoir adhesive sequence loaded with a transdermal active substance.

A short chain vegetable-oil-based polyol with a MW=700 and having two functionalities is associated with the isocyanate of example 1. It is produced by ALBERDINGK BOLEY and marketed under the brand ALBODRY®.

The following are available:
a short chain ether-based polyol, more precisely, of type (PPG), MW=400 and having two functionalities. This polyol is produced by DOW CHEMICAL and marketed under the brand VORANOL P400.
a long chain polycarbonate-base polyol of MW=1000 and having two functionalities. This product is produced by UBE CHEMICAL and marketed under the brand ETERNACOLL® PH100.
a chain elongator of MW=90 and having two functionalities known under the chemical name of 1,4-Butanediol
a degazing agent BYK® 066.
a perfume marketed by CREATIONS & PARFUM under the brand BSG®51774.
a lipophilic anhydrous caffeine preparation with a slimming down action formulated by AB7 INDUSTRIES S.A.

The same equipment as that used in example 1 is available.

Procedure: The operations are performed according to a procedure similar to that of example 1 and the catalyst solution is prepared like in example 1.

A)—Preparation of the <<Reservoir>> Phase Solution of a Stoichiometry OH/NCO=1

The following are successively introduced in the reactor:
  1.57 parts by weight of the catalyst solution;
  0.86 of a part by weight of the chain elongator;
  0.39 of a part by weight of the degazing agent;
  19.61 parts by weight of the perfume, called active substance, and
  49.87 parts by weight of the short chain polyol (ALBODRY®)
All this is agitated at 1300 rpm for 30 seconds. The polyol complex loaded with the active substance is obtained;
In the said polyol complex, 27.71 parts by weight of isocyanate are added according to a stoichiometry OH/NCO=1, and agitated at 1300 rpm for 30 seconds. The phase solution loaded with the perfume active substance is obtained;
The said phase solution obtained is poured in the mould over a thickness of 1 mm, and the polymerisation reaction is allowed to continue to constitute the <<Reservoir>> sequence.

B)—Preparation of the <<Support-Barrier>> Phase Solution of a Stoichiometry OH/NCO=1

In parallel with operation A), the polyol complex is modified by associating in the reactor:
  1.95 parts by weight of the catalyst solution;
  0.49 of a part by weight of the degazing agent and
  52.52 parts by weight of the short chain polyol (VORANOL® P400)
All this is agitated at 1300 rpm for 30 seconds. The polyol complex is obtained.
In the said polyol complex obtained, 45.04 parts by weight of isocyanate are added according to a stoichiometry OH/NCO=1, and agitated at 1300 rpm for 30 seconds. The phase solution is obtained;
The said phase solution obtained is poured to a thickness of 1 mm on the <<Reservoir>> sequence which has exceeded the pot life, but which has not attained the demoulding time;
The polymerisation reaction is allowed to continue in order to constitute the <<Support-Barrier>> sequence.

C)—Preparation of the <<Reservoir-Adhesive>> Phase Solution of a Stoichiometry OH/NCO=1.5

In parallel with operation B), the polyol complex is modified by associating in the reactor:
  1.78 parts by weight of the catalyst solution;
  0.44 of a part by weight of the degazing agent;
  8.89 parts by weight of the lipophilic anhydrous caffeine preparation, called active substance, and
  72.35 parts by weight of the long chain polyol (ETERNACOLL® PH100).
All this is agitated at 1300 rpm for 30 seconds. The polyol complex loaded with the active substance is obtained;
In the said polyol complex, 16.54 parts by weight of isocyanate are added according to a stoichiometry OH/NCO=1.5, and agitated at 1300 rpm for 30 seconds. The phase solution loaded with the active substance is obtained;

The said phase solution obtained is poured to a thickness of 1 mm on the <<Support-Barrier>> sequence which has exceeded the pot life, but has not attained the demoulding time;

Polymerisation is allowed to continue in order to constitute the <<Reservoir-Adhesive>> sequence;

The patch obtained is removed from the mould when the demoulding time of the said <<Reservoir-Adhesive>> sequence is attained.

The well-being and slimming-down patch obtained is very flexible and adhesive on the side of the <<Reservoir-Adhesive>> sequence loaded with caffeine. The said patch has a thickness of 3 mm. The matrix loaded with the active substances of the said patch has the particularity of diffusing by volatility the perfume which is in the <<Reservoir>> sequence; diffusing transdermally the caffeine formulation which is in the <<Reservoir-Adhesive>> sequence when the said patch is applied to the skin on the side of the <<Reservoir-Adhesive>> sequence. The <<Support-Barrier>> sequence inserted between the two <<Reservoir>> sequences plays the role of a barrier preventing both the caffeine to migrate to the <<Reservoir>> sequence and the perfume to migrate to the <<Reservoir-Adhesive>> phase. The said patch is intended for the human slimming-down treatment in human.

Example 5

Codling Moth Attracting Self-Adhesive Plate in a Matrix with a <<Reservoir/Support-Barrier/Adhesive>> Profile This example illustrates the making of a monopolymer matrix offering a self-adhesive function of a plate on only one side and a profile organised into a succession of three sequences: a reservoir sequence loaded with pheromone, a support barrier sequence and an adhesive sequence.

A long chain ether-based polyol, more precisely, of type PTMEG, with MW=2000 and having two functionalities, is associated with the isocyanate of example 1. This polyol is produced by FORMOSA ASAHI SPANDEX and marketed under the brand P2000 BX®.

The following are available:
a chain elongator of MW=149 and having three functionalities, the TRIETHANOLAMINE produced by BASF.
a degazing agent BYK® 066
a lipophilic preparation containing a sexual pheromone produced by SHIN-ETSU.

The same equipment is available as that used in example 1.

Procedure: The operations are performed according to a procedure similar to that of example 1 and the catalyst solution is prepared like in example 1.

A)—Preparation of the <<Reservoir>> Phase Solution of a Stoichiometry OH/NCO=1

The following are introduced in the reactor in this order:
1.91 parts by weight of the catalyst solution;
0.78 of a part by weight of the chain elongator;
0.48 of a part by weight of the degazing agent;
1.91 parts by weight of the pheromone, called active substance, and
79.48 parts by weight of the long chain polyol of operation A).

All this is agitated at 1300 rpm for 30 seconds. The polyol complex loaded with the pheromone is obtained.

In the said polyol complex obtained, 15.43 parts by weight of isocyanate are added according to a stoichiometry OH/NCO=1, and agitated at 1300 rpm for 30 seconds. The phase solution loaded with the active substance is obtained;

The said phase solution obtained is poured to a thickness of 1 mm to constitute the <<Reservoir>> sequence.

B)—Preparation of the <<Support-Barrier>> Phase Solution of a Stoichiometry OH/NCO=1

In parallel with operation A)—, the polyol complex is modified by associating in the reactor:
1.95 parts by weight of the catalyst solution;
0.49 of a part by weight of the degazing agent and
59.65 parts by weight of the long chain polyol All this is agitated at 1300 rpm for 30 seconds. The polyol complex is obtained;

In the said polyol complex, 37.92 parts by weight of isocyanate are added according to a stoichiometry OH/NCO=1, and agitated at 1300 rpm for 30 seconds. The phase solution is obtained;

The said phase solution obtained is poured to a thickness of 1 mm on the <<Barrier>> sequence which has exceeded the pot life, but which has still not attained the demoulding time, and the polymerisation reaction is allowed to continue in order to constitute the <<Support-Barrier>> sequence.

C)—Preparation of the <<Adhesive>> Phase Solution of a Stoichiometry OH/NCO=1.5

In parallel, the polyol complex is modified by associating in the reactor:
1.95 parts by weight of the catalyst solution;
0.49 of a part by weight of the degazing agent and
68.53 parts by weight of the long chain polyol of operation A).

All this is agitated at 1300 rpm for 30 seconds. The polyol complex is obtained;

In the said polyol complex, 29.04 parts by weight of isocyanate are added according to a stoichiometry OH/NCO=1.5, and agitated at 1300 rpm for 30 seconds. The phase solution is obtained;

The said phase solution obtained is poured to a thickness of 1 mm on the <<Support-Barrier>> sequence which has exceeded the pot life, but which has not yet exceeded the demoulding time;

Polymerisation is allowed to continue in order to constitute the <<Adhesive>> sequence;

The thus obtained plate is removed from the mould when the demoulding time of the said <<Adhesive>> sequence is attained.

The 3 mm thick plate obtained is flexible and is self-adhesive on the side of the <<Adhesive>> sequence. The said plate glued to the branches of apple trees is intended for the treatment of these trees against the codling moth by diffusing the sexual pheromone in a controlled amount in order to create confusion in the codling moth males.

Example 6

Perfumed Plate with Self-Adhesive <<Suction Cups>> in a Matrix with a <<Adhesive/Support-Reservoir>> Profile This example illustrates the making of a monopolymer matrix loading in active substance offering a self-adhesive function with adhesive suction cups supported on the discontinuous side of the <<Adhesive>> sequence according to a profile organised into a succession of two sequences: an adhesive sequence and a reservoir support sequence loaded with the active substance. The 0.5 mm high suction cups allow air to circulate under the reservoir support.

A long chain polyol, ALCUPOL®C-3531, is associated with the isocyanate of example 1.

A perfume marketed by CREATIONS & PARFUM under the brand SHG® 61562 is available.

The same equipment is available as used in example 1, as well as a polypropylene mould consisting of an open circular disk of a 15 cm diameter and 1 cm thickness, within which five wells are distributed, each with a diameter of 1.5 cm and to a depth of 0.5 mm.

Procedure: The operations are performed according to a procedure similar to that of example 1 and the catalyst solution is prepared like in example 1.

A)—Preparation of the <<Adhesive>> Phase Solution of a Stoichiometry OH/NCO=1.5

The following are successively introduced in the reactor:
  1.96 parts by weight of the catalyst solution;
  91.50 parts by weight of the long chain polyol.
All this is agitated at 1300 rpm for 30 seconds. The polyol complex is obtained;
In the said polyol complex obtained, 6.54 parts by weight of isocyanate are added according to a stoichiometry OH/NCO=1.5, and then agitated at 1300 rpm for 30 seconds. The phase solution is obtained;
The said phase solution obtained is only poured in the mould wells to a depth of 5 mm;
The polymerisation reaction is allowed to continue in order to constitute the <<Adhesive>> sequence.

B)—Preparation of the <<Reservoir-Support>> Phase Solution of a Stoichiometry OH/NCO=1

In parallel with operation A), the polyol complex is modified by associating in the reactor:
  1.64 parts by weight of the catalyst solution;
  16.39 parts by weight of the perfume, called active substance;
  74.03 parts by weight of the long chain polyol of operation A).
All this is agitated at 1300 rpm for 30 seconds. The polyol complex loaded with the active substance is obtained;
In the said polyol complex obtained, 7.93 parts by weight of isocyanate are added according to a stoichiometry OH/NCO=1, and agitated at 1300 rpm for 30 seconds. The phase solution loaded with the active substance is obtained;
The said phase solution obtained is poured to a thickness of 1 cm on the <<Adhesive>> sequence which has exceeded the pot life, but which has still not attained the demoulding time;
Polymerisation reaction is allowed to continue in order to constitute the <<Reservoir-Support>> sequence;
The thus obtained plate is removed from the mould when the demoulding time of the said <<Reservoir-Adhesive>> sequence is attained.

The 1 cm thick perfuming plate obtained is very flexible and presents 5 mm long self-adhesive spikes. The said plate is intended to perfume a room by diffusion of the perfume on both sides of the <<Reservoir-Support>> sequence.

The invention claimed is:

1. A process for preparing a multifunctional sequenced cast polyurethane matrix at room temperature consisting of the following steps:
  a) preparing the polyol complex 1, which consists of mixing the catalyst solution, the various additives, the volatile or transdermally penetrating active substance and the polyol(s);
  b) preparing the phase solution 1, which consists of mixing the polyol complex 1 obtained in step a) with isocyanate according to the stoichiometry corresponding to the function of a sequence 1 selected from the group consisting of a reservoir sequence or a reservoir-adhesive sequence, the stoichiometry being of 1 for the reservoir sequence, and greater than 1 for the reservoir-adhesive sequence;
  c) pouring the phase solution 1 of step b) in a mould to obtain a sequence 1 in conformity with the desired thickness of the sequence 1;
  d) preparing a polyol complex 2, which consists of mixing the catalyst solution, the various additives, and the polyol(s);
  e) preparing a phase solution 2, which consists of mixing the polyol complex 2 obtained in step d) with isocyanate according to the stoichiometry corresponding to the function of a sequence 2 selected from the group consisting of a support sequence, a support-barrier sequence, an adhesive sequence, the stoichiometry being of 1 for the support sequence, a support-barrier sequence, and greater than 1 for the adhesive sequence;
  f) pouring the phase solution 2 obtained in step e) in the mould to obtain the sequence 2 as defined in step e) on the sequence 1 obtained in step c), which has exceeded a pot life, but which has still not attained the demoulding time, in order to allow a copolymerisation at the interface of the two sequences;
  g) repeat the steps a) to f) to obtain the multifunctional matrix, the last and/or the first sequence according to the matrix's selected profile being a sequence at least adhesive in which the phase solution of the polyol complex with the isocyanate has a stoichiometry greater than 1;
  h) let the polymerisation of the last sequence terminate up to its demoulding time and therefore up to the polymerisation of the whole of the matrix;
  i) remove the formed multifunctional sequenced polyurethane matrix from the mould;
  j) package the polyurethane matrix in a sealed, tight, and impermeable pocket.

2. The process according to claim 1 wherein the main reactive materials of polymerisation are:
  a) the isocyanate selected from among the isocyanates with at least two functionalities of an aromatic or aliphatic structure;
  b) the polyol(s) selected from among those with at least two functionalities, with a long chain or a short chain, based on polyesters, polyethers, polythioethers, polyacetals, polyesteramides, polycarbonates, naturally hydrolysed or modified vegetable oils, or the mixture thereof.

3. The process according to claim 1, wherein the polyols can be replaced according to the same reactivity considerations as with isocyanate by polyamines having at least two amine functionalities selected from among the aliphatic or aromatic polyetheramines and under some conditions by water.

4. The process according to claim 1, wherein:
  a) the catalyst is selected from the group consisting of organometallic solutions, preferably bismuth, and tertiary amine solutions;

b) the degazing agent is selected from the group consisting of polymers of polysiloxanes, the polymers of methyl alkyl polysiloxanes and a mixture thereof;
c) the plasticizer is selected from the group consisting of the solutions of ester benzoate, the alkyl phosphate and phthalates;
d) the impermeabilizer is selected from resins of low molecular weight or inert loads;
e) the ultraviolet stabilizers and the other stabilizers are selected from the group consisting of phenolic antioxidants type BHT (Butylated hydroxytoluene) or BHA (Butylated hydroxyanisol), the redox antioxidants type HALS (Hindered Amine Light Stabilizer) with piperidine pattern, the phosphite antioxidants, the formamidine antioxidants, the benzotriazole antioxidants, the benzophenone antioxidants or a mixture of them; and
f) a dye.

* * * * *